US009987505B2

(12) United States Patent
Jolesz et al.

(10) Patent No.: US 9,987,505 B2
(45) Date of Patent: Jun. 5, 2018

(54) METHOD FOR MODIFYING GLOMERULAR PERMEABILITY AND FUNCTION WITH FOCUSED ULTRASOUND

(75) Inventors: Ferenc Jolesz, Brookline, MA (US); Krisztina Fischer, Brookline, MA (US); Nathan McDannold, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1775 days.

(21) Appl. No.: 13/058,945

(22) PCT Filed: Aug. 20, 2009

(86) PCT No.: PCT/US2009/054471
§ 371 (c)(1),
(2), (4) Date: May 3, 2011

(87) PCT Pub. No.: WO2010/022239
PCT Pub. Date: Feb. 25, 2010

(65) Prior Publication Data
US 2011/0208095 A1 Aug. 25, 2011

Related U.S. Application Data

(60) Provisional application No. 61/090,401, filed on Aug. 20, 2008, provisional application No. 61/091,136, filed on Aug. 22, 2008.

(51) Int. Cl.
*A61B 8/00* (2006.01)
*A61N 7/00* (2006.01)
*A61B 90/00* (2016.01)

(52) U.S. Cl.
CPC .......... *A61N 7/00* (2013.01); *A61B 2090/374* (2016.02); *A61N 2007/0039* (2013.01)

(58) Field of Classification Search
USPC .................................................. 600/439, 411
See application file for complete search history.

(56) References Cited

U.S. PATENT DOCUMENTS

2002/0082501 A1* 6/2002 Emery .......................... 600/443
2002/0123702 A1 9/2002 Cho
2003/0036697 A1 2/2003 Ottobon
2004/0163655 A1* 8/2004 Gelfand et al. ............... 128/898
(Continued)

OTHER PUBLICATIONS

"Miller et al.," "Bioeffects Considerations for Diagnostic Ultrasound Contrast Agents," J Ultrasound Med 2008; 27:611-632 (Apr. 2008).*
(Continued)

*Primary Examiner* — Patricia Park
(74) *Attorney, Agent, or Firm* — Quarles & Brady LLP

(57) ABSTRACT

A method for noninvasively changing the permeability of a region of a subject that includes a desired tissue is provided. More specifically, low-power focused ultrasound (FUS) is employed to alter the permeability of the glomerulus so as to alter the glomerular ultrafiltration coefficient. By employing FUS after administering a microbubble contrast agent to a subject, glomerular filtration is temporarily increased and the clearance of larger molecules, which are normally not filtered by the kidney, is allowed. This method offers new treatment opportunities for renal disease management.

4 Claims, 7 Drawing Sheets

(56) References Cited

U.S. PATENT DOCUMENTS

2007/0073197 A1    3/2007  Frausnitz
2009/0088623 A1*  4/2009  Vortman et al. .............. 600/411

OTHER PUBLICATIONS

"Salmon et al.," "Evidence of restriction of fluid and solute movement across the glomerular capillary wall by the subpodocyte space," American Journal of Physiology, Renal Physiology, 293:F1777-1786, Sep. 2007.*

The International Search Report dated Mar. 3, 2010 for International Application No. PCT/US2009/054471.

* cited by examiner

METHOD FOR MODIFYING GLOMERULAR PERMEABILITY AND FUNCTION WITH FOCUSED ULTRASOUND

CROSS-REFERENCE TO RELATED APPLICATIONS

This application claims the benefit of, and herein incorporates by reference in their entirety, PCT International Application PCT/US2009/054471 filed on Aug. 20, 2009, U.S. Provisional Patent Application Ser. No. 61/090,401 filed on Aug. 20, 2008, and entitled "Method for Increasing Blood-To-Urine Barrier Permeability with Focused Ultrasound," and further claims the benefit of, and herein incorporates by reference in its entirety, U.S. Provisional Patent Application Ser. No. 61/091,136 filed on Aug. 22, 2008, and entitled "Method for Increasing Blood-To-Urine Barrier Permeability with Focused Ultrasound."

STATEMENT REGARDING FEDERALLY SPONSORED RESEARCH

This invention was made with United States government supports awarded by the following agency: National Institutes of Health R01EB003268, R33EB000705, and U41RR019703. The United States government has certain rights in this invention.

BACKGROUND OF THE INVENTION

The field of the invention is ultrasound methods and systems. More specifically, the field of the invention is noninvasive ultrasonic techniques for changing glomerular permeability in order to modify kidney ultrafiltration. In general, the present invention also relates to a therapeutic use of ultrasound that can be monitored using existing imaging techniques There are a number of modes in which ultrasound can be used to produce images of objects. The ultrasound transmitter may be placed on one side of the object and the sound transmitted through the object to the ultrasound receiver placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction," "backscatter," or "echo" mode).

There are a number of well known backscatter methods for acquiring ultrasound data. In the so-called "A-scan" method, an ultrasound pulse is directed into the object by the transducer and the amplitude of the reflected sound is recorded over a period of time. The amplitude of the echo signal is proportional to the scattering strength of the refractors in the object and the time delay is proportional to the range of the refractors from the transducer. In the so-called "B-scan" method, the transducer transmits a series of ultrasonic pulses as it is scanned across the object along a single axis of motion. The resulting echo signals are recorded as with the A-scan method and their amplitude is used to modulate the brightness of pixels on a display. The location of the transducer and the time delay of the received echo signals locates the pixels to be illuminated. With the B-scan method, enough data are acquired from which a two-dimensional image of the refractors can be reconstructed. Rather than physically moving the transducer over the subject to perform a scan it is more common to employ an array of transducer elements and electronically move an ultrasonic beam over a region in the subject.

Ultrasonic transducers for medical applications are constructed from one or more piezoelectric elements sandwiched between a pair of electrodes. Such piezoelectric elements are typically constructed of lead zirconate titanate ("PZT"), polyvinylidene diflouride ("PVDF"), or PZT ceramic/polymer composite. The electrodes are connected to a voltage source, and when a voltage is applied, the piezoelectric elements change in size at a frequency corresponding to that of the applied voltage. When a voltage pulse is applied, the piezoelectric element emits an ultrasonic wave into the media to which it is coupled at the frequencies contained in the excitation pulse. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is disposed to the rear of the piezoelectric element to absorb ultrasonic waves that emerge from the back side of the element so that they do not interfere.

When used for ultrasound imaging, the transducer typically has a number of piezoelectric elements arranged in an array and driven with separate voltages ("apodizing"). By controlling the time delay (or phase) and amplitude of the applied voltages, the ultrasonic waves produced by the piezoelectric elements ("transmission mode") combine to produce a net ultrasonic wave focused at a selected point. By controlling the time delay and amplitude of the applied voltages, this focal point can be moved in a plane to scan the subject.

The same principles apply when the transducer is employed to receive the reflected sound ("receiver mode"). That is, the voltages produced at the transducer elements in the array are summed together such that the net signal is indicative of the sound reflected from a single focal point in the subject. As with the transmission mode, this focused reception of the ultrasonic energy is achieved by imparting separate time delay (and/or phase shifts) and gains to the echo signal received by each transducer array element.

As indicated above, there are a number of electronic methods for performing a scan using a transducer having an array of separately operable elements. These methods include linear array systems and phased array systems.

A linear array system includes a transducer having a large number of elements disposed in a line. A small group of elements are energized to produce an ultrasonic beam that travels away from the transducer, perpendicular to its surface. The group of energized elements is translated along the length of the transducer during the scan to produce a corresponding series of beams that produce echo signals from a two-dimensional region in the subject. To focus each beam that is produced, the pulsing of the inner elements in each energized group is delayed with respect to the pulsing of the outer elements. The time delays determine the depth of focus which can be changed during scanning. The same delay factors are applied when receiving the echo signals to provide dynamic focusing during the receive mode.

The second common form of ultrasonic imaging is referred to as phased array sector scanning ("PASS"). Such a scan is comprised of a series of measurements in which all of the elements of a transducer array are used to transmit a steered ultrasonic beam. The system then switches to receive mode after a short time interval, and the reflected ultrasonic wave is received by all of the transducer elements. Typically, the transmission and reception are steered in the same direction, $\theta$, during each measurement to acquire data from a series of points along a scan line. The receiver is dynamically focused at a succession of ranges, R, along the scan line as the reflected ultrasonic waves are received. A series of measurements are made at successive steering angles, $\theta$, to scan a pie-shaped sector of the subject. The time required to conduct the entire scan is a function of the time required to make each measurement and the number of measurements required to cover the entire region of interest at the desired resolution and signal-to-noise ratio. For example, a total of 128 scan lines may be acquired over a sector spanning 90 degrees, with each scan line being steered in increments of 0.70 degrees.

The same scanning methods may be used to acquire a three-dimensional image of the subject. The transducer in such case is a two-dimensional array of elements which steer a beam throughout a volume of interest or linearly scan a plurality of adjacent two-dimensional slices.

Various ultrasound generated acoustic-mechanical effects can induce transient changes in vascular permeability and function. For example, low intensity focused ultrasound ("FUS"), whether alone or combined with the administration of a gas microbubble-based ultrasound contrast agent, has been shown to enhance the permeability of biological membranes. This phenomenon has been utilized in methods that seek to enhance the delivery of drugs or genes. Furthermore, other previous methods have shown that ultrasound bursts combined with a microbubble contrast agent can result in temporary disruption, or breaking down, of the blood-brain barrier. While the exact mechanism for the blood-brain barrier disruption is unknown, it appears that it may result from enhancement of the permeability of the endothelial cells or a widening of the junctions between the endothelial cells. In addition physiological changes induced or triggered by the ultrasound bursts employed in FUS may play a pivotal role. For example, electron microscopy studies have shown active vesicular transport as well as passive diffusion through widened tight junctions. During the sonications, temporary vasospasm associated with the ultrasound bursts has also been observed with in vivo microscopy.

The glomerulus is another vascular structure that functions as a barrier, and in its case, as one between the blood and the urine. Glomerular ultrafiltration is a hemodynamically regulated event that is modulated though the glomerular barrier. This barrier has physical properties that can be dynamically changed. These include the thickness of the glomerular basement membrane ("GBM") and the slit diaphragm's spread of the epithelial layer. Such physical properties may be dynamically changed in order to increase, or decrease, the glomerular ultrafiltration coefficient, as needed to reach the filtration pressure equilibrium.

More specifically, the glomerulus is an ultrafiltration structure capable of filtering a large volume of plasma while retaining macromolecules in the circulation. The GBM and the cellular layers are responsible for maintaining this function. Recent studies on healthy animals, such as those described by W. M. Deen, et al., in "Structural Determinants of Glomerular Permeability," *Am J Physiol Renal Physiol*, 2001; 281(4): F579-F596, have suggested that the glomerular ultrafiltration coefficient can dynamically change as a function of time to ensure the filtration pressure equilibrium and the stability of the glomerular ultrafiltration. Previous studies that examined the permselectivity of the glomerular membrane and the sieving of different size Dextrans, such as those described by R. L. Chang, et al., in "Permselectivity of the Glomerular Capillary Wall: Studies of Experimental Glomerulonephritis in the Rat Using Neutral Dextran," *J Clin Invest*, 1976; 57(5):1272-1286, have found that filtration of 70,000 Dalton ("Da") Dextran to the urinary space is extremely limited under normal circumstances.

The glomerular barrier plays a fundamental role in filtration impairment. For example, a decrease in the glomerular ultrafiltration is thought to originate in a decreased hydraulic permeability of the capillary wall (i.e., a substantial decrease in the glomerular ultrafiltration coefficient), a decreased surface area within the glomerulus, a decreased number of functioning glomeruli, or some combination of these factors, as described by A. B., Fogo in "Mechanisms of Progression of Chronic Kidney Disease," *Pediatr Nephrol*, 2007; 22(12): 2011-2022.

Patients with severe heart failure who are resistant to conventional kidney therapies have very high one-year mortality. Noninvasively increasing the GFR in these patients would cause excess water and salt to be gradually removed without compromising blood pressure and could help reverse sympathetic and rennin-angiotensin overactivity. The ability to alter GFR in a patient would also provide a temporary time-window to increase the filtration of even large molecules, such as toxins like Shiga toxin produced during *E. coli* 0157:H7 infection, which are normally not cleared by the kidney. Such a method could also enhance the efficiency of the detoxification of smaller molecules, such as Lithium, through a temporary GFR increase.

It would therefore be desirable to provide a non-invasive method for altering glomerular ultrafiltration by either directly modifying the membranes involved in ultrafiltration or otherwise triggering a vasoactive response using a mechanical stimulus that is highly targeted at the glomeruli. Such a stimulus would be a powerful tool that could open doors for novel renal therapies and provide a new method to study kidney function and disease.

SUMMARY OF THE INVENTION

The present invention overcomes the aforementioned drawbacks by providing a method for non-invasively and dynamically changing the permeability of the glomerulus so as to alter the glomerular ultrafiltration coefficient. More specifically, the present invention provides a method for noninvasively altering ultrafiltration in the kidney by employing low frequency focused ultrasound ("FUS") after administering a microbubble contrast agent to a subject. Such a method does not breakdown the cellular composition of the glomeruli, but instead enhances the function of the dynamically changing filtration properties of the glomerular barrier.

One aspect of the present invention provides a method for low-power focused ultrasound bursts combined with a microbubble contrast agent in order to affect the renal barrier function. By employing FUS with microbubbles, glomerular filtration is temporarily increased and the clearance of larger molecules that are normally not filtered by the kidney is allowed. The mechanical interactions of ultrasound with glomerular vessels modulate renal ultrafiltration by employing 260 kHz FUS bursts at three acoustic power levels (0.4, 0.9, and 1.7 watts) in the presence of microbubble ultrasound contrast agent. Changes in glomerular permselectivity are evaluated by measuring the clearance rates of 3,000 and 70,000 Da fluorescent Dextrans and the relative protein/creatinine ratio. Tubular function is also assessed. Approximately a 1.5 fold elevation in both relative creatinine and 3,000 Da Dextran clearances, and a 2 fold elevation in the relative 70,000 Da Dextran clearance and urine flow rate as provided when practicing the present invention. The fact that such a large molecule agent (70,000 Da Dextran) is cleared and that this clearance occurs with a rapid onset suggests that the functional changes in the glomerular filtration involve changes in the glomerular membrane properties. Thus, glomerular ultrafiltration is modified with simultaneous application of ultrasound and microbubble contrast agents. This method offers new treatment opportunities for renal disease management.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
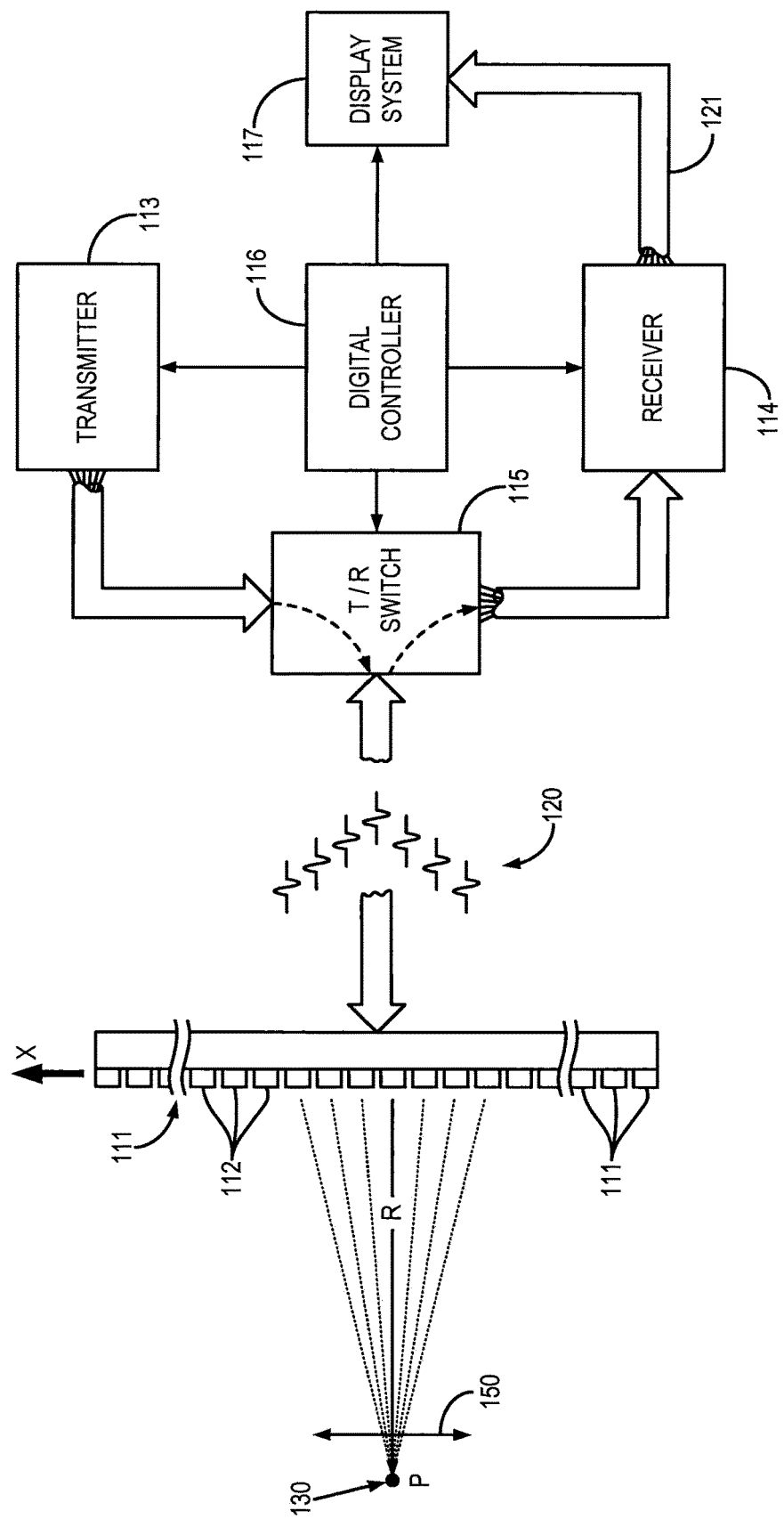
FIG. 1 is a block diagram of an ultrasonic system which employs the present invention.

Referring particularly to FIG. 1, an ultrasonic imaging system includes a transducer array 111 comprised of a plurality of separately driven elements 112 which each produce a burst of ultrasonic energy when energized by a pulse produced by a transmitter 113. The ultrasonic energy reflected back to the transducer array 111 from the subject under study is converted to an electrical signal by each transducer element 112 and applied separately to a receiver 114 through a set of switches 115. The transmitter 113, receiver 114, and the switches 115 are operated under the control of a digital controller 116 responsive to the commands input by the human operator. A complete scan is performed by acquiring a series of echoes in which the switches 115 are set to their transmit position, the transmitter 113 is gated on momentarily to energize each transducer element 112, the switches 115 are then set to their receive position, and the subsequent echo signals produced by each transducer element 112 are applied to the receiver 114. The separate echo signals from each transducer element 112 are combined in the receiver 114 to produce a single echo signal which is employed to produce a line in an image on a display system 117. Exemplary transducer array 111 designs include an air-backed spherically curved transducer array, such as the one described by K. Hynynen, et al., in "Thermal Effects of Focused Ultrasound on the Brain: Determination with MR Imaging," *Radiology*, 1997; 204:247-253.

Figure 2:
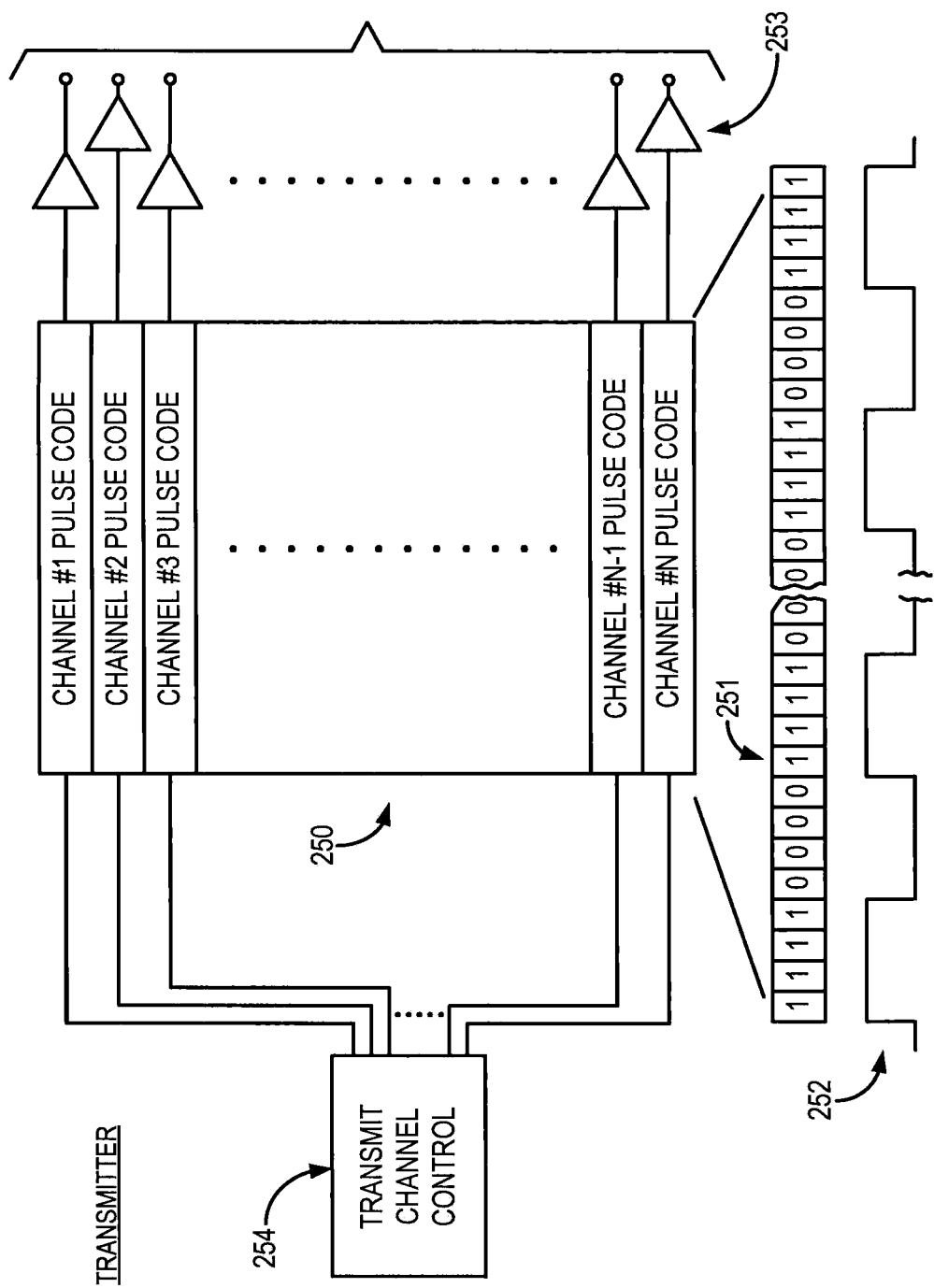
FIG. 2 is a block diagram of a transmitter which forms a part of the system of FIG. 1.

Referring particularly to FIG. 2, the transmitter 113 includes a set of channel pulse code memories which are indicated collectively at 250. Each pulse code memory 250 stores a bit pattern 251 that determines the frequency of the ultrasonic pulse 252 that is to be produced. This bit pattern is read out of each pulse code memory 250 by a master clock and applied to a driver 253 which amplifies the signal to a power level suitable for driving the transducer 111. In the example shown in FIG. 2, the bit pattern is a sequence of four "1" bits alternated with four "0" bits to produce a 5 megahertz ("MHz") ultrasonic pulse 252. The transducer elements 111 to which these ultrasonic pulses 252 are applied respond by producing ultrasonic energy.

As indicated above, to steer the transmitted beam of the ultrasonic energy in the desired manner, the pulses 252 for each of the N channels must be produced and delayed by the proper amount. These delays are provided by a transmit control 254 which receives control signals from the digital controller 116. When the control signal is received, the transmit control 254 gates a clock signal through to the first transmit channel 250. At each successive delay time interval thereafter, the clock signal is gated through to the next channel pulse code memory 250 until all the channels to be energized are producing their ultrasonic pulses 252. Each transmit channel 250 is reset after its entire bit pattern 251 has been transmitted and the transmitter 113 then waits for the next control signal from the digital controller 116. By operating the transmitter 113 in this manner, ultrasonic energy can be focused on a focal point 130, P, when practicing the herein described method. This focal point can be steered electronically with the appropriate changes to the timing delays provided by the transmit control 254. The term "focal point," as referred to herein, includes not only a single point object in the usual sense, but also a general region-of-interest to which ultrasound energy is delivered in a substantially focused manner.

Figure 3:
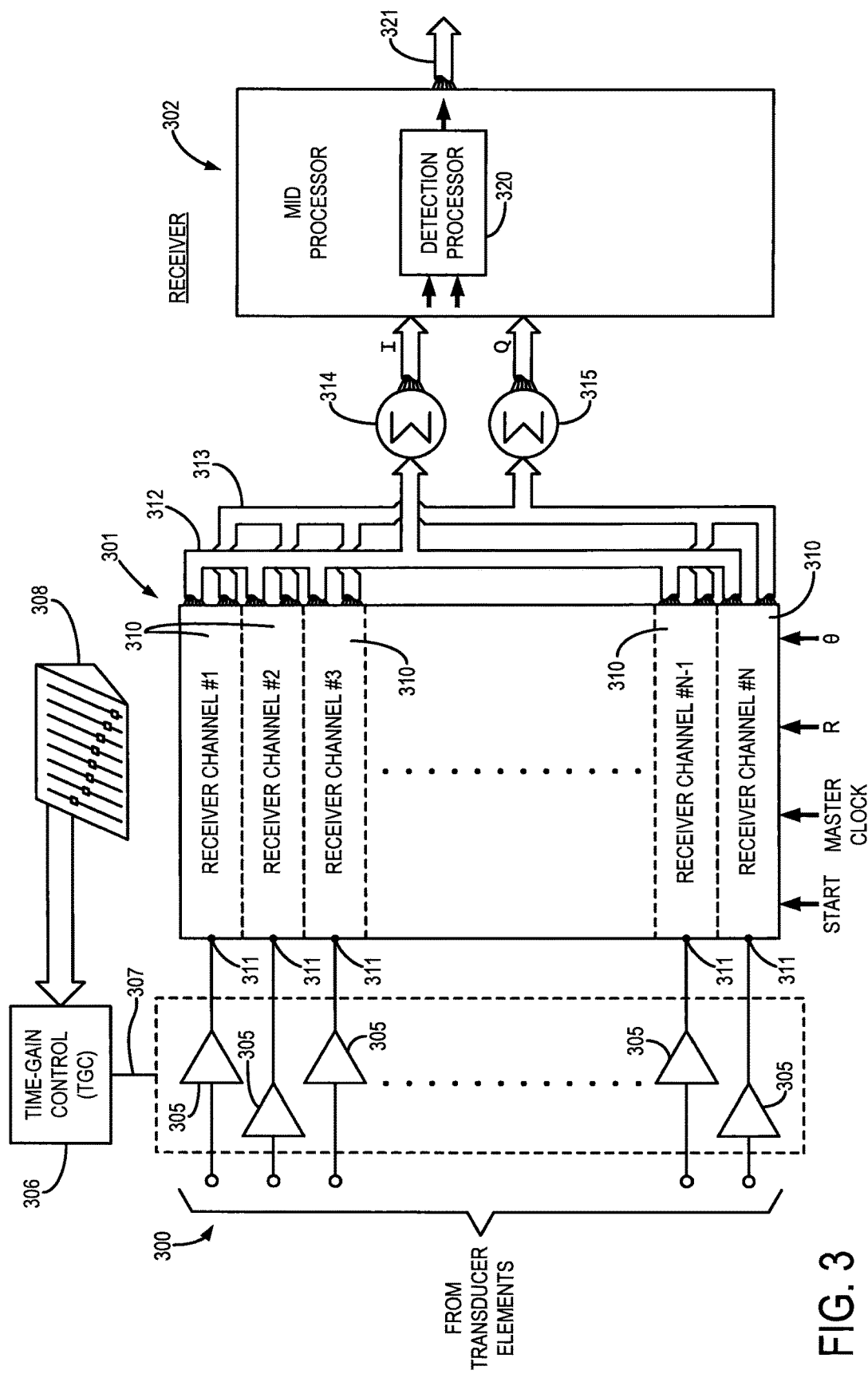
FIG. 3 is a block diagram of a receiver which forms a part of the system of FIG. 1.

Referring particularly to FIG. 3, the receiver 114 is comprised of three sections: a time-gain control ("TGC") section 300, a beam forming section 301, and a mid processor 302. The time-gain control section 300 includes an amplifier 305 for each of the N receiver channels and a time-gain control circuit 306. The input of each amplifier 305 is connected to a respective one of the transducer elements 112 to receive and amplify the echo signal which it receives. The amount of amplification provided by the amplifiers 305 is controlled through a control line 307 that is driven by the time-gain control circuit 306. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range, R. This amplification is controlled by the operator who manually sets TGC linear potentiometers 308 to values which provide a relatively uniform brightness over the entire range of the scan. The time interval over which the echo signal is acquired determines the range from which it emanates, and this time interval is divided into segments by the TGC control circuit 306. The settings of the potentiometers are employed to set the gain of the amplifiers 305 during each of the respective time intervals so that the echo signal is amplified in ever increasing amounts over the acquisition time interval.

The beam forming section 301 of the receiver 114 includes N separate receiver channels 310. Each receiver channel 310 receives the analog echo signal from one of the TGC amplifiers 305 at an input 311, and it produces a stream of digitized output values on an I bus 312 and a Q bus 313. Each of these I and Q values represents a sample of the echo signal envelope at a specific range, R. These samples have been delayed in the manner described above such that when they are summed at summing points 314 and 315 with the I and Q samples from each of the other receiver channels 310, they indicate the magnitude and phase of the echo signal reflected from a point, P, located at range, R, on the ultrasonic beam.

Referring still to FIG. 3, the mid processor section 302 receives the beam samples from the summing points 314 and 315. The I and Q values of each beam sample is a digital number which represents the in-phase and quadrature components of the magnitude of the reflected sound from a point, P. The mid processor 302 can perform a variety of calculations on these beam samples, where choice is determined by the type of image to be reconstructed. For example, if a conventional magnitude image is to be produced, a detection process indicated at 320 is implemented in which a digital magnitude, M, is calculated from each beam sample according to:

$$M=\sqrt{I^2+Q^2}$$ Eqn. (1);

and output at 321.

The detection processor 320 may also implement correction methods that, for example, examine the received beam samples and calculate corrective values that can be used in subsequent measurements by the transmitter 113 and receiver 114 to improve beam focusing and steering. Such corrections are necessary, for example, to account for the non-homogeneity of the media through which the sound from each transducer element travels during a scan.

Figure 4:
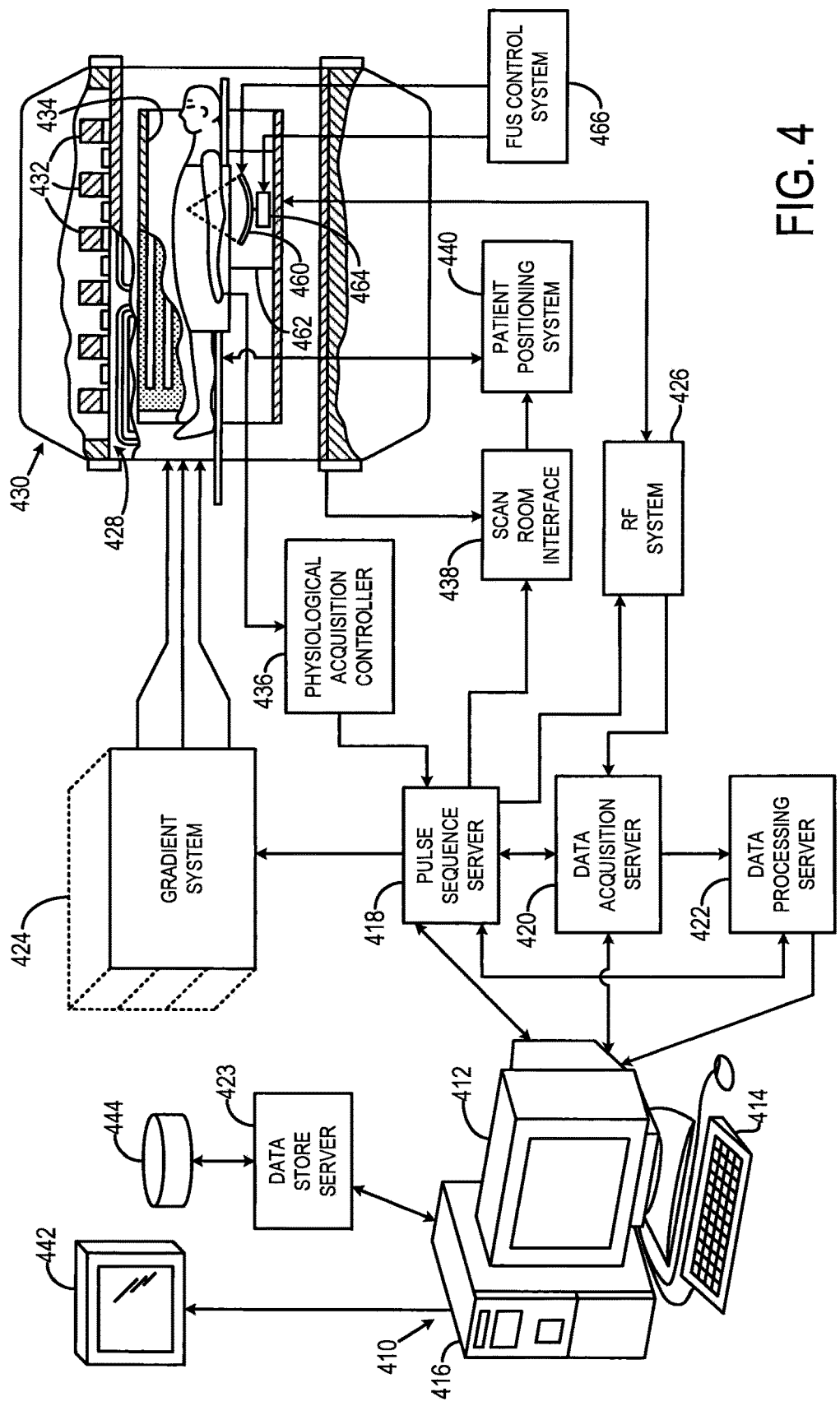
FIG. 4 is a block diagram of a magnetic resonance imaging ("MRI") system that includes an integrated focused ultrasound ("FUS") transducer.

Referring particularly now to FIG. 4, the herein described method can be employed, for example, with a magnetic resonance imaging ("MRI") system that is utilized to guide the focused ultrasound energy, as will be described below in detail. Methods that utilize an MRI system for the monitoring or control of FUS applications are commonly referred to as MR guided focused ultrasound ("MRgFUS"). The MRI system includes a workstation 410 having a display 412 and a keyboard 414. The workstation 410 includes a processor 416 that is a commercially available programmable machine running a commercially available operating system. The workstation 410 provides the operator interface that enables scan prescriptions to be entered into the MRI system. The workstation 410 is coupled to four servers: a pulse sequence server 418; a data acquisition server 420; a data processing server 422, and a data store server 423. The workstation 410 and each server 418, 420, 422 and 423 are connected to communicate with each other.

The pulse sequence server 418 functions in response to instructions downloaded from the workstation 410 to operate a gradient system 424 and an RF system 426. Gradient waveforms necessary to perform the prescribed scan are produced and applied to the gradient system 424 that excites gradient coils in an assembly 428 to produce the magnetic field gradients $G_x$, $G_y$, and $G_z$ used for position encoding MR signals. The gradient coil assembly 428 forms part of a magnet assembly 430 that includes a polarizing magnet 432 and a whole-body RF coil 434.

RF excitation waveforms are applied to the RF coil 434 by the RF system 426 to perform the prescribed magnetic resonance pulse sequence. Responsive MR signals detected by the RF coil 434 or a separate local coil (not shown in FIG. 4) are received by the RF system 426, amplified, demodulated, filtered and digitized under direction of commands produced by the pulse sequence server 418. The RF system 426 includes an RF transmitter for producing a wide variety of RF pulses used in MR pulse sequences. The RF transmitter is responsive to the scan prescription and direction from the pulse sequence server 418 to produce RF pulses of the desired frequency, phase and pulse amplitude waveform. The generated RF pulses may be applied to the whole body RF coil 434 or to one or more local coils or coil arrays (not shown in FIG. 4).

The RF system 426 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2}$$ Eqn. (2);

and the phase of the received MR signal may also be determined:

$$\phi = \tan^{-1}\left(\frac{Q}{I}\right).$$ Eqn. (3)

The pulse sequence server 418 also optionally receives patient data from a physiological acquisition controller 436. The controller 436 receives signals from a number of different sensors connected to the patient, such as ECG signals from electrodes or respiratory signals from a bellows. Such signals are typically used by the pulse sequence server 418 to synchronize, or "gate", the performance of the scan with the subject's respiration or heart beat.

The pulse sequence server 418 also connects to a scan room interface circuit 438 that receives signals from various sensors associated with the condition of the patient and the magnet system. It is also through the scan room interface circuit 438 that a patient positioning system 440 receives commands to move the patient to desired positions during the scan.

The digitized MR signal samples produced by the RF system 426 are received by the data acquisition server 420. The data acquisition server 420 operates in response to instructions downloaded from the workstation 410 to receive the real-time MR data and provide buffer storage such that no data is lost by data overrun. In some scans the data acquisition server 420 does little more than pass the acquired MR data to the data processor server 422. However, in scans that require information derived from acquired MR data to control the further performance of the scan, the data acquisition server 420 is programmed to produce such information and convey it to the pulse sequence server 418. For example, during prescans MR data is acquired and used to calibrate the pulse sequence performed by the pulse sequence server 418. Also, navigator signals may be acquired during a scan and used to adjust RF or gradient system operating parameters or to control the view order in which k-space is sampled. And, the data acquisition server 420 may be employed to process MR signals used to detect the arrival of contrast agent in a magnetic resonance angiography ("MRA") scan. In all these examples the data acquisition server 420 acquires MR data and processes it in real-time to produce information that is used to control the scan.

The data processing server 422 receives MR data from the data acquisition server 420 and processes it in accordance with instructions downloaded from the workstation 410. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 422 are conveyed back to the workstation 410 where they are stored. Real-time images are stored in a data base memory cache (not shown) from which they may be output to operator display 412 or a display 442 that is located near the magnet assembly 430 for use by attending physicians. Batch mode images or selected real time images are stored in a host database on disc storage 444. When such images have been reconstructed and transferred to storage, the data processing server 422 notifies the data store server 423 on the workstation 410. The workstation 410 may be used by an operator to archive the images, produce films, or send the images via a network to other facilities.

The MRI system includes a patient table with an integrated ultrasound transducer 460. The ultrasound transducer 460 is operable to perform the herein described method for enhancing renal filtration. The ultrasound transducer 460 includes an array of ultrasound transducer elements that are arrayed, for example, similar to the systems described in U.S. Pat. Nos. 6,613,004 and 6,735,461.

The ultrasound transducer 460 is housed in a housing 462 that is filled with an acoustically conductive fluid, such as degassed water or a similar acoustically transmitting fluid. The ultrasound transducer 460 is preferably connected to a positioning system 464 that moves the transducer 460 within the housing 462, and consequently mechanically adjusts the focal zone of the transducer 460. For example, the positioning system 464 may be configured to move the transducer 460 within the housing 462 in any one of three orthogonal directions and to pivot the transducer 460 about a fixed point within the housing 462 to change the angle of the transducer 460 with respect to a horizontal plane. When the angle of the transducer 460 is altered, the focal distance of the focal zone is controlled electronically by changing the phase and/or amplitude of the drive signals provided to the transducer 460, as described, for example, in U.S. Pat. No. 6,613,004. These drive signals are provided to the ultrasound transducer by an FUS control system 466 that includes drive circuitry in communication with the ultrasound transducer 460 and a controller that is in communication with the positioning system 464 and drive circuitry.

The top of the housing 462 includes a flexible membrane that is substantially transparent to ultrasound, such as a Mylar, polyvinyl chloride ("PVC"), or other plastic materials. In addition, a fluid-filled bag (not shown) is generally provided along the top of the patient table that can conform easily to the contours of a patient placed on the table.

Figure 5:
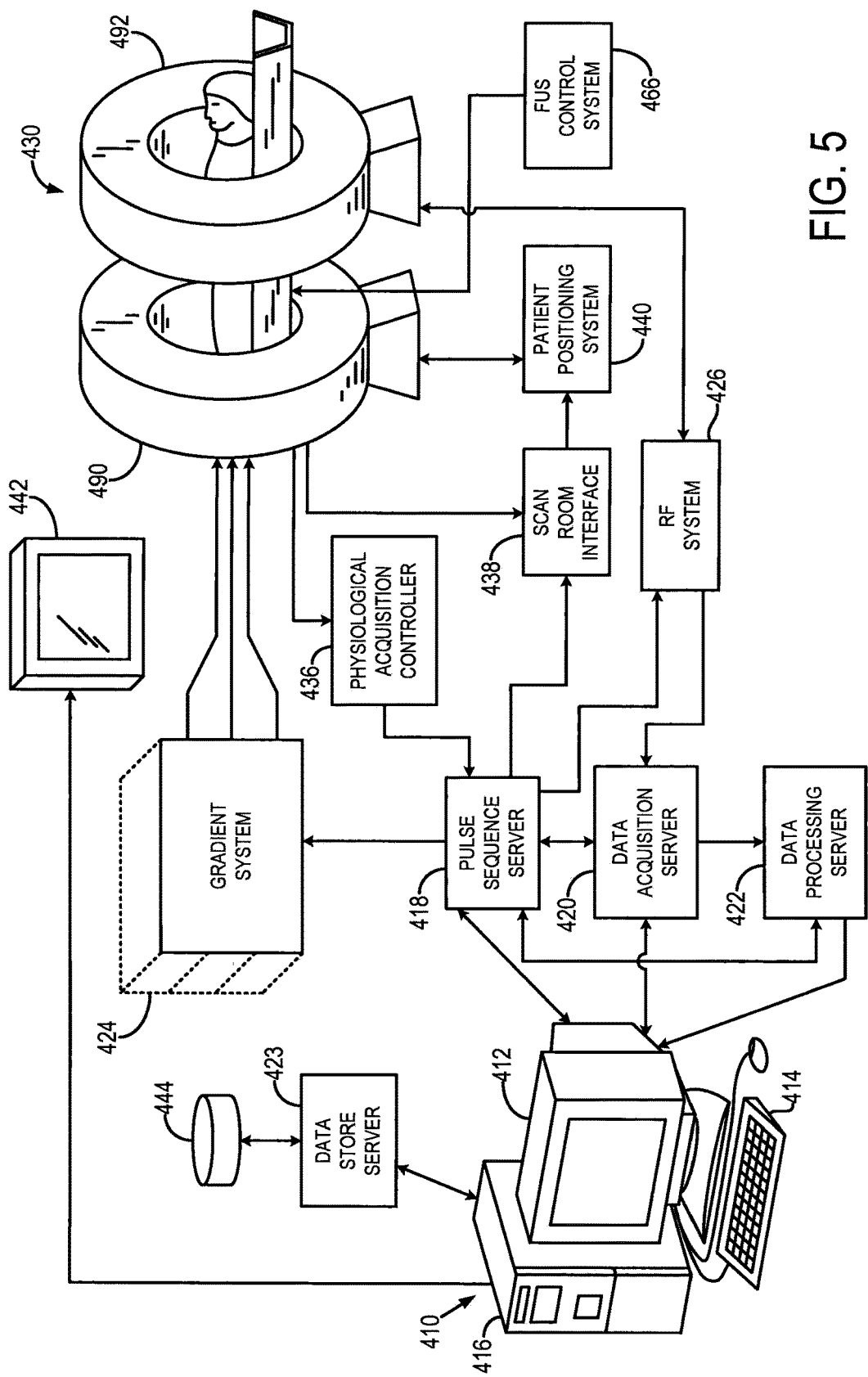
FIG. 5 is a block diagram of an MRI system that is configured to provide access to a subject during examination.

While an MRI system that employs a patient table with an integrated ultrasound transducer, such as the one described above, may be used to implement the invention, another configuration of an MRI system, which is designed to allow access by a physician, can also be employed. Referring particularly to FIG. 5, when an intra-operative MR imaging procedure is conducted a patient is placed in the magnet system 430 and a region of interest in the patient is aligned near the system isocenter located between the two, spaced magnet rings 490 and 492. A physician standing between magnet rings 490 and 492 has unrestricted access to the region of interest in the patient. During the procedure the patient may move, or be moved by the physician. An ultrasonic transducer (not shown) connected to a focused ultrasound ("FUS") system 466 may be manipulated by the physician to treat a selected region of the patient and the images produced on display 442 may be used by the physician to help aim the FUS device and to determine when treatment is completed.

It will become apparent from the following description that any of the above described MRI systems can be employed when practicing the present invention, with the choice of MRI system related to the nature of FUS system employed. In this manner, the MRI systems are utilized for such applications including the monitoring of subject temperature in the region where FUS is applied and measuring renal function to assess the efficacy of the herein described method.

The mechanisms by which ultrasound and a microbubble-based contrast agent cause glomerular ultrafiltration enhancement are not precisely known. Indeed, several biological effects could result from the ultrasound interaction with the microbubbles and the subsequent acoustic-mechanical effects. For example, the microbubbles may oscillate within the acoustic field and grow in size via rectified diffusion. At sufficient acoustic pressures they can collapse during the positive pressure cycle, a phenomenon known as inertial cavitation, and produce shock waves, high-velocity micro jets, free radicals, and high local temperatures. In addition, other possible effects include acoustic streaming of the fluid surrounding the bubbles, which could result in large shear stresses at the vessel walls, or direct impulse on the vessels through the oscillation of the microbubble or the acoustic radiation force. Microbubble oscillations may also produce sharp temporary pressure changes within the vessel. The most violent event that can be induced is inertial cavitation, which may cause hemorrhage and tissue damage. However, when practicing the herein described method, hemorrhaging that would likely result from inertial cavitation is not observed, suggesting that inertial cavitation is not a dominant acoustic-mechanical effect.

The magnitude of the filtration enhancement is related to the level of acoustic power applied to the subject. Exemplary acoustic power levels include those in the range of 0.4-1.7 watts ("W"). Likewise, proteinuria appears to depend on the acoustic power and is not present when lower acoustic power values, such as 0.4 W, are employed. This may indicate tubular proteinuria and if so, tubular damage may be involved when higher power levels are applied to the subject. The herein described method is further able to provide a temporary time window to increase the filtration of large molecules that are normally not cleared by the kidney. Indeed, the power-dependent nature of the modified GFR suggests that higher volume of the treated kidney induces a more significant result in the GFR modification. This, in turn, provides evidence that the ultrasound-induced GFR modification is a local, membrane related effect, not a global effect that results overall changes in kidney function. The observed power dependent increase in podocyte slit distance, that is through the contraction of the podocytes, also suggests that the FUS induced GFR increase is related to a change in the glomerular barrier's physical properties. The increased podocyte distance induces larger filtration surface that may result directly in the modification in GFR.

Figure 6:
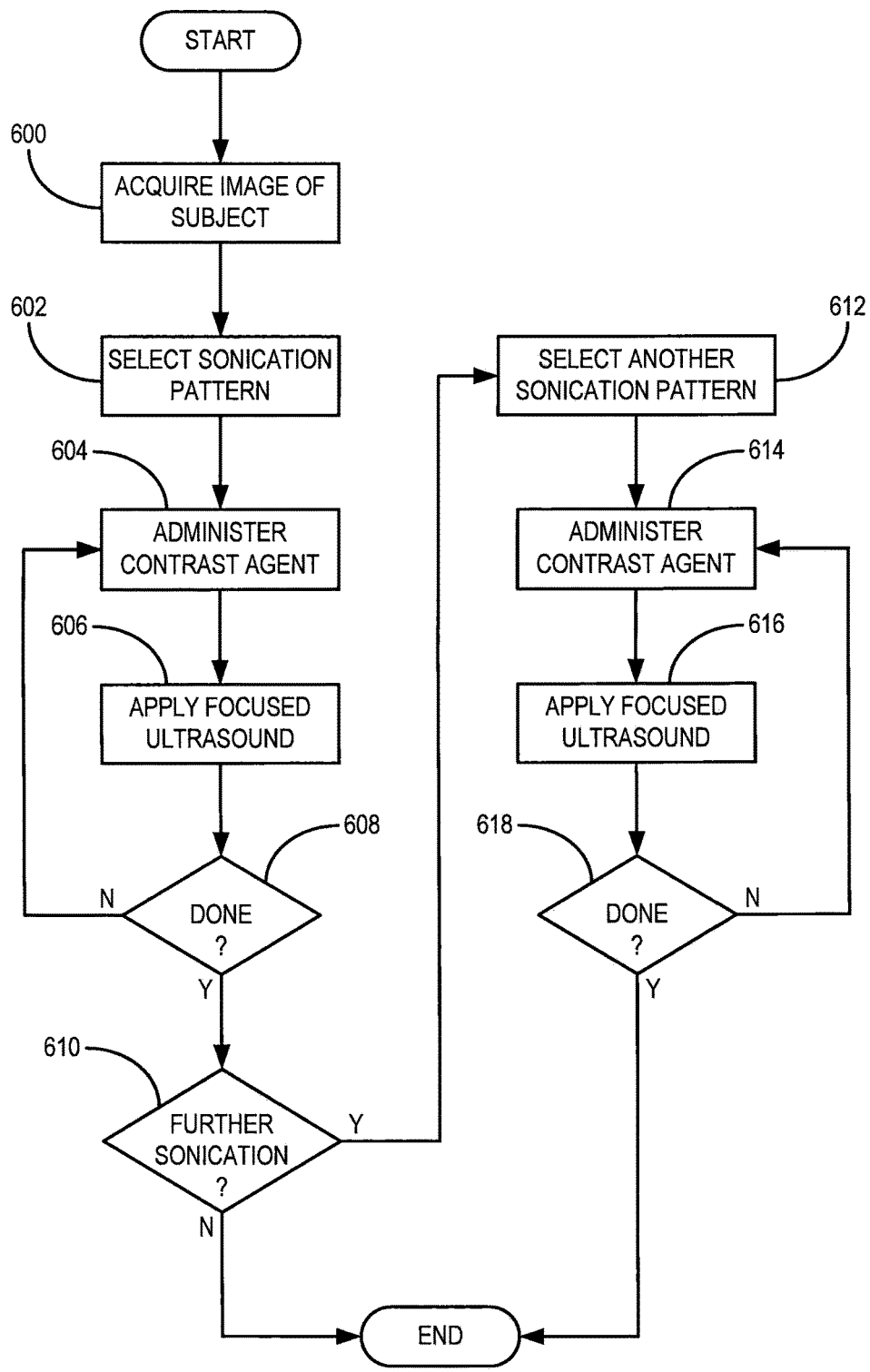
FIG. 6 is a flowchart setting forth the steps of a method for enhancing the glomerular filtration rate ("GFR") of a subject with focused ultrasound ("FUS")
Figure 7:
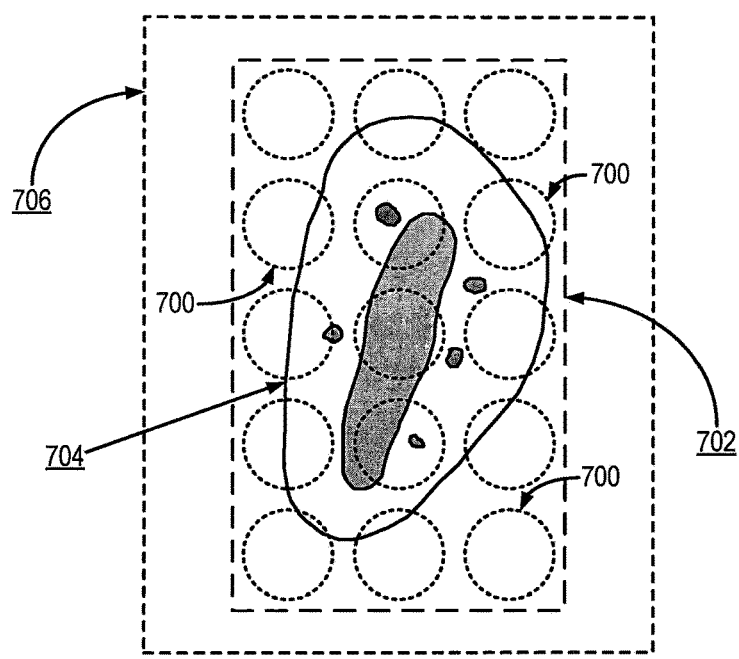
FIG. 7 is a pictorial representation of an exemplary sonication pattern that defines locations in a focal plane to which focused ultrasound energy is applied in the method of FIG. 6.
Figure 8:
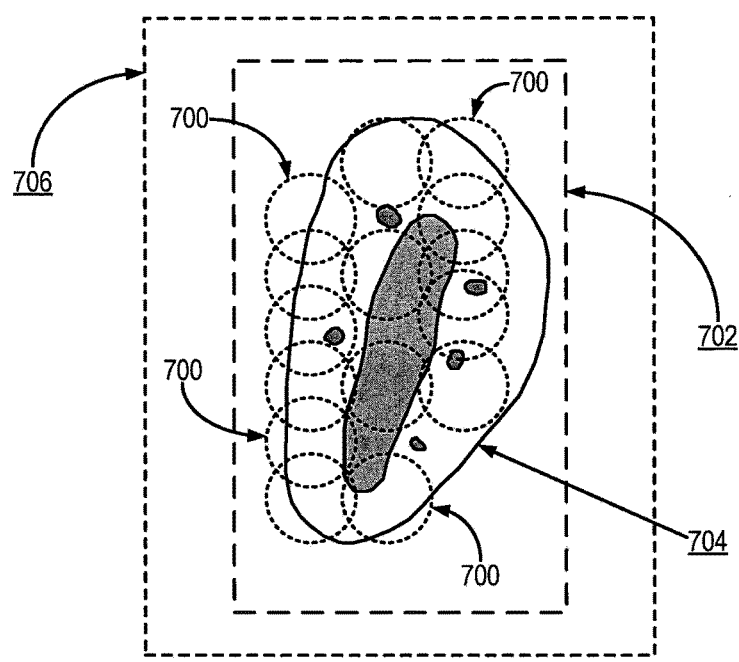
FIG. 8 is a pictorial representation of another exemplary sonication pattern that defines locations in a focal plane to which focused ultrasound energy is applied in the method of FIG. 6.

Referring now to FIG. 6, the steps of an exemplary method for enhancing the filtration properties of a subject's kidney with focused ultrasound ("FUS") are provided. The method beings with the acquisition of an image of the subject undergoing examination, as indicated at step 600. For example, when employing a standalone ultrasound system to provide the FUS energy, this same system can be operated to acquire an image of the subject, as described above. When practicing the method with guidance from an MRI system, the MRI system can be employed to acquire images of the subject. In any case, the acquired images are subsequently employed to select a desired pattern of sonication, as indicated at step 602. For example, a focal plane containing the kidney is located and the locations in this plane to which FUS energy is to be applied are selected. An exemplary sonication pattern is illustrated in FIG. 7, in which the locations (dashed circles) 700 to which FUS energy is to be applied are distributed substantially uniformly in a region-of-interest 702 that includes the kidney 704. As described above, the region-of-interest 702 is located within a focal plane 706. An alternate sonication pattern is illustrated in FIG. 8, in which the locations 700 to which FUS energy is to be applied are distributed more specifically over the kidney 704. Aside from selecting the locations to which FUS energy is to be applied, the focal length of the FUS energy is also selected. By way of example, when selecting a long focal length, ultrasound effects occur predominantly throughout an entire target region within the focal spot. For example, the target region may include a kidney and the long focal length will promote the altered ultrafiltration throughout the thickness of the kidney that is within the focal spot.

When the sonication pattern is selected, an ultrasound contrast agent is administered to the subject, as indicated at step 604. In the alternative, however, a contrast agent need not be administered to effect the filtration properties of the kidney. Exemplary ultrasound contrast agents include, for example, Definity® (Bristol-Myers Squibb Medical Imaging, N. Billerica, Mass.), which is administered intravenously to the subject preceding each sonication and at a dosage of, for example, 10 microliters per kilogram of body weight. Next, FUS energy is applied to the subject in accordance with the selected sonication pattern, as indicated at step 606. By way of example, each sonication utilized includes thirty pulses with a duration of 10 milliseconds ("ms") at a repetition frequency of 1 hertz ("Hz") and with an acoustic energy frequency of 260 kilohertz ("kHz"). Targets are located approximately 1 centimeter ("cm") deep into the kidney in a single plane. For example, as illustrated in FIG. 7, fifteen sonications are delivered at 1 cm intervals to cover the extent of the target region to each of fifteen different locations 700. A decision is made whether the desired amount of sonication has been applied to the subject using the prescribed sonication pattern, as indicated at decision block 608. If the sonication is not done, another bolus of contrast agent is administered to the subject and FUS energy is applied to the next location in the sonication pattern. This process can also be repeated, for example, at different acoustic power levels. Exemplary acoustic power levels include 0.4, 0.9, and 1.7 W. These exposure levels corresponded to an estimated spatial peak, temporal peak negative pressure amplitudes of 0.30, 0.41, and 0.58 MPa in the focal plane, assuming an acoustic attenuation of 6.5 Np/m/MHz.

After the desired amount of sonication has been applied to the subject using the prescribed sonication pattern, a determination is made as to whether further sonication is desired, as indicated at decision block 610. For example, the application of FUS energy to the subject using a second sonication pattern may be desired. In this instance, a different sonication pattern is selected, as indicated at step 612. For example, the sonication pattern illustrated in FIG. 7 is selected at step 602 and the sonication pattern illustrated in FIG. 8 is selected at step 612. As is described above, the method then proceeds with the administration of an ultrasound contrast before each application of FUS energy to the subject, as indicated at steps 614 and 616, respectively. Likewise, a determination is made at decision block 618 as to whether the desired amount of sonication has been applied to the subject using the sonication pattern prescribed at step 612. When the desired amount of sonication has been applied to the subject, the method is completed.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for modifying glomerular permeability in a subject's kidney with an ultrasound system, the steps comprising:
   a) administering an ultrasound contrast agent to the subject; and
   b) applying an acoustic energy, with the ultrasound system, to temporarily modify glomerular filtration in the kidney during a passage of the ultrasonic contrast agent through the subject's kidney.

2. The method as recited in claim 1 in which the applied acoustic energy is focused ultrasound energy.

3. The method as recited in claim 2 in which the focused ultrasound energy is applied to produce a pressure having a desired amplitude in a focal region of the focused ultrasound such that a slit distance between podocytes in a glomerulus is temporarily modified.

4. The method as recited in claim 3 in which the desired amplitude of the produced pressure is a spatial-peak, temporal-peak negative pressure amplitude having a value in the range of 0.3-0.58 megapascal.

* * * * *